United States Patent [19]

Strand

[11] Patent Number: 4,700,997

[45] Date of Patent: Oct. 20, 1987

[54] ELECTRICAL CONNECTOR

[75] Inventor: Jerome E. Strand, Hudson, Wis.

[73] Assignee: Minnesota Mining and Manufacturing Company, St. Paul, Minn.

[21] Appl. No.: 930,494

[22] Filed: Nov. 14, 1986

[51] Int. Cl.$^4$ ............................................. H01R 9/07
[52] U.S. Cl. ................................. 439/372; 439/499; 439/836; 439/729; 439/863; 439/370
[58] Field of Search ............ 339/75 R, 75 M, 75 MP, 339/17 F, 176 MF, 200 R, 253 R, 255 P, 273 R, 273 F; 128/798, 303.13

[56] References Cited

U.S. PATENT DOCUMENTS

| | | | |
|---|---|---|---|
| 446,564 | 2/1891 | Bacon | 24/536 |
| 1,536,688 | 5/1925 | Osborn | 339/75 P |
| 3,094,365 | 6/1963 | Chamberlain et al. | 339/75 R |
| 3,447,122 | 5/1969 | Beck | 339/273 R |
| 3,475,717 | 10/1969 | Lane | 339/75 |
| 3,624,590 | 11/1971 | Bolduc | 339/75 R |
| 3,725,853 | 4/1973 | McKeown et al. | 339/252 R |
| 3,824,529 | 7/1974 | Dorrell | 339/99 |
| 3,842,394 | 10/1974 | Bolduc | 339/75 R |
| 4,061,408 | 12/1977 | Bast et al. | 339/75 R |
| 4,393,584 | 7/1983 | Bare et al. | 29/877 |
| 4,401,356 | 8/1983 | Bare | 339/258 R |
| 4,550,961 | 11/1985 | Aicher et al. | 339/14 R |
| 4,629,271 | 12/1986 | Awano | 339/75 MP |

Primary Examiner—John McQuade
Attorney, Agent, or Firm—Donald M. Sell; James A. Smith; Mary M. Allen

[57] ABSTRACT

An electrical connector for removably attaching a flat electrode to a conducting cable is shown. Flat, conductive upper and lower jaws are connected at the rear by flexible, resilient spring means, and are spaced apart at the front. The jaws are mounted within a housing, and are surmounted by a slide actuator having a finger movable member passing through a slot in a housing roof. The actuator slides on a guide means having a front planar surface and a rear planar surface higher than the front planar surface, the two planar surfaces connected by a ramp in a transition area. In the forward position, the actuator compresses the jaws together on the surfaces of the flat electrode to tightly hold the electrode in a locked conductive connection, and simple finger movement of the actuator releases the electrode.

12 Claims, 16 Drawing Figures

ELECTRICAL CONNECTOR

FIELD OF THE INVENTION

This invention relates to electrical connectors useful for removable attachment to flat biomedical electrodes. In particular, this invention relates to a small, lightweight connector which will connect to, firmly hold, and easily disconnect from a flat biomedical electrode for maintaining an electrical connection to a conductive cable leading to a recorder, meter, current or voltage source, or other device.

BACKGROUND OF THE INVENTION

Flat biomedical electrodes are used in various applications. A common use is for transcutaneous monitoring of biological and physiological electrical potential associated with muscular activity. Flat electrodes are also commonly used for grounding patients during electrosurgery. The thickness of such electrodes may be less than 1 millimeter, or as great as 5 millimeters or more.

In medical and other applications, several differing types of connectors are used for conducting the electrical signal from the flat electrode to the measuring, recording, or grounding device. For best results and ease of operation, connectors desirably provide firm conductive connections, yet are readily removed from the electrode. In electrocardiographic applications, flat electrodes may be attached to patients for short-term diagnoses. Long term monitoring is also common, where the electrode is operatively connected to a monitoring device for several days. Unless the electrical connections are tight the patient's movements may stress the connecting cables sufficiently to pull the connectors from the electrodes. In addition, the connector should be held immobile on the surface of the electrode, since relative movement therebetween may produce artifacts in a signal.

One type of connector currently used in the medical field for attachment to flat electrodes is the well-known alligator clip, which depends on a small spring to provide the closing force. The holding force is transmitted through teeth on the jaws, rather than through flat surfaced jaws. Alligator clips tend to move on electrodes, and provide little surface contact for holding electrodes.

Another connector commonly used is the snap connector, in which a female member is snapped onto a circular male button. The female member may easily rotate on the male button and thereby produce artifacts on an electrical trace.

Bolduc, U.S. Pat. No. 3,624,590, shows a clamp for a flat grounding plate electrode, in which a spring provides the clamping force. Projections on one of the clamping jaws pass through holes in the electrode to lock it in place.

Lane, U.S. Pat. No. 3,475,717, describes an electrical connector for printed circuit boards in which a spring member in each side of the circuit board is actuated by a movable member. Contact between the springs and the circuit board is limited to a downward projecting edge of the springs.

Another form of connector is shown in Bast et al., U.S. Pat. No. 4,061,408. An integral electrically conductive sheet is motivated downward to a closed position by a lever arm for holding a plate electrode. The holding force is exerted along a narrow strip where the rounded end of the lever contacts the conductive sheet.

Bolduc, U.S. Pat. No. 3,842,394, shows an electrical connector for a grounding plate electrode in which the jaws are closed by a hand actuated clamp moving against a coil spring. The clamp handle may be turned to adjust the holding force, and a projection may be used to pierce the electrode to hold it in place.

SUMMARY OF THE INVENTION

The present invention is an electrical connector for removably attaching a flat electrode to a conducting cable. The connector has clamp means, a slide actuator, a housing, and a closure member. The clamp means has a flat upper jaw and a flat lower jaw for holding the electrode. The jaws have front and rear ends, and are comprised of conductive resilient flexible sheet material such as spring metal. The inner facing surfaces are spaced from each other at the front end for accepting and retaining an electrode. The jaws are joined at the rear end by flexible resilient spring means to normally maintain the jaws in an open position, and are adapted for pivotal downward movement of the upper jaw toward the lower jaw to an electrode retaining position. In this position, the facing surfaces of the jaws resist movement of the flat electrode. The jaws are adapted for conductive attachment to a conducting cable by soldering, welding, crimping or other method.

The slide actuator serves to motivate the upper jaw downward from the open position to the closed position. The slide actuator has a generally flat slide plate with a forwardly directed, downwardly sloped front edge which contacts a slide actuator guide means formed in the housing. The slide plate is surmounted by a finger-movable member which moves forward to close the jaws and lock the connector onto the electrode and backward to open the jaws and unlock the connector from the electrode.

The clamp means and slide actuator are contained in the housing which has a front opening. The jaws of the clamp means are oriented so that their front ends are adjacent the front opening of the housing for receiving and holding the electrode.

The housing has a base, roof, and two side members connecting the corresponding lateral edges of the base and roof. The base supports of the lower jaw of the clamp means. The roof has a rearward opening slot through which the finger-movable member of the slide actuator passes. Thus, the slide actuator is moved forwardly and rearwardly within the slot in the roof.

The housing also includes a slide actuator guide means located at or below the underside of the roof. It has front and rear generally planar surfaces separated by a transition area. The transition area is forwardly-directed ramp angled downwardly from the rear surface to the front surface. A first forward movement of the slide actuator forces the actuator downward along the guide means ramp so that the lower surface of the slide plate of the actuator contacts the upper jaw and motivates it downwardly, generally pivotally about the rear end of the clamp means. The upper jaw is thus moved downward to the electrode retaining position. Further forward movement of the slide actuator along the front planar lower surface of the slide actuator guide means frictionally locks the slide actuator into its electrode retaining position.

Abutting the rear of the housing and attached to it is a closure member. When attached to the housing, the closure member retains the clamp means and the slide actuator within the housing. The closure member has an aperture though which a cable is passed for attachment to the clamp means.

In a preferred embodiment the front generally planar surface and the transition area of the slide actuator guide means comprises a plurality of ribs integral with and depending from the roof of the housing. The ribs are aligned parallel with slot in the roof.

Another preferred embodiment includes at least one opening in the rear end of the jaw and at least one jaw positioning means extending upwardly from the base of the housing. The opening in the jaw and the post are aligned so that the post rests in the opening to maintain the clamp means within the housing.

In an alternative embodiment the outer surface of the base includes a transverse ridge to facilitate manual gripping of the connector.

The preferred clamps means has the forward edge of the lower jaw bent downwardly and the forward edge of the upper jaw bent upwardly. These upward and downward bends serve as ramps to facilitate insertion of an electrode between the jaws.

The preferred clamp means also has means on the jaw surfaces for resisting movement of an electrode surface. The surfaces may be rough grained or they may have rearwardly projecting teeth on one or both surfaces. Most preferred are electrically conductive rearwardly projecting teeth.

In an alternative embodiment the housing has slots in each side member. The slots are adjacent the sides of the clamp means. They allow use of the connector with flat electrodes that are wider than the width of the connector.

The connector may also include clamp retaining means connected to the closure member. The clamp retaining means abut the rear end of the jaws when the closure member is attached to the housing to prevent forward and rearward movement of the clamp means within the housing.

When assembled, the connector provides significantly improved holding power because of the wedging action of the slide actuator between the slide actuator guide means and the upper jaw. The holding power is achieved with minimal height, and the connector may be very small without sacrificing its holding strength. Because of the relatively large jaw area which compresses the electrode, the electrode is less likely to tear, when compared to a connector which simply uses a member passing through a hole in the electrode to lock it in place. The electrode of the present invention is prevented from easy movement within the jaws, avoiding possible artifacts in electrocardiographic use. This new connector is easily and readily attached and removed by simple finger movement.

Unlike some presently used connectors, both jaws are conductive, so that the connector may be attached to an electrode having a conductive surface on only one side with either side up.

BRIEF DESCRIPTION OF THE DRAWINGS

FIG. 16 is a side view of the housing and closure member of a further embodiment of this invention.

DETAILED DESCRIPTION OF THE INVENTION

Figure 1:
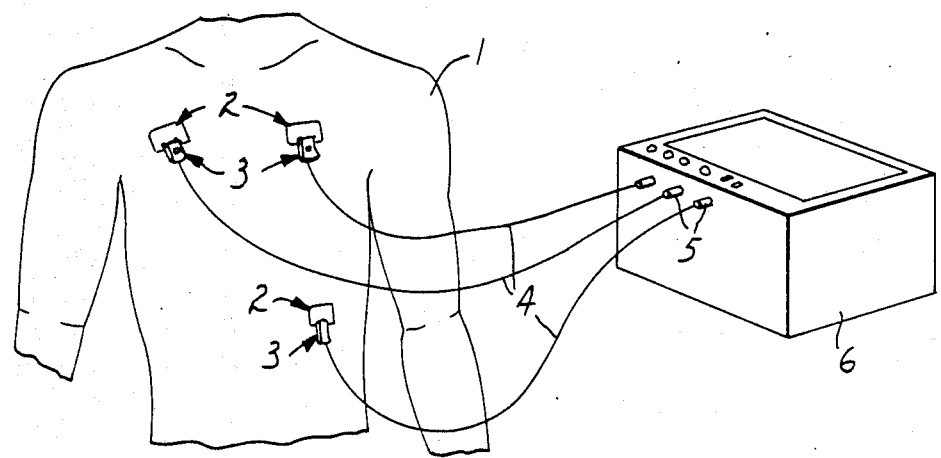
FIG. 1 is a diagrammatic view showing the connector of the invention linking a biomedical electrode used on a patient to an ECG/EKG unit.

Turning now to FIG. 1, the instant invention is illustrated as used for electrocardiographic diagnosis of a human patient. Flat electrodes 2 are attached to the patient by suction, adhesive, tape, or other means to measure the electrical potential at several locations. Connectors 3 of this invention are attached to cables 4 and are removably attached to flat electrodes 2. The other end 5 of each cable is connected to an electrocardiographic recorder 6 for providing a time trace of the potential.

Figure 2:
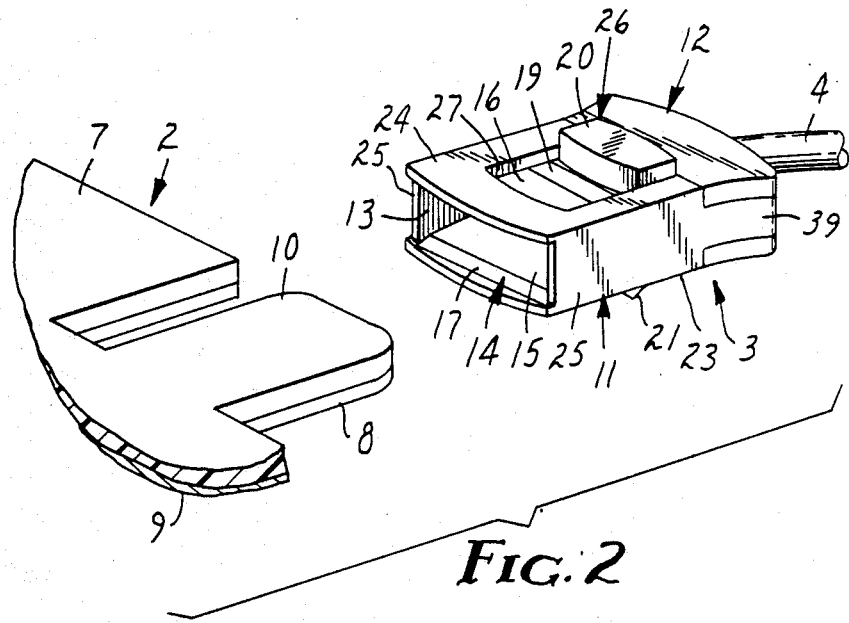
FIG. 2 is a perspective view of one embodiment of the invention together with a breakaway view of a tabbed flat electrode.

FIG. 2 shows an embodiment of the connector 3 in detail, together with a portion of a flat tabbed electrode 2 for use in electrocardiography. This particular electrode is shown with backing 7 having a conductive member 8 attached to its lower side and an adhesive layer 9 for attaching the electrode to a patient's skin. The backing 7 may be a flexible material such as a foamed elastomer, a film, a non-woven web or other material. A tab 10 of electrode 2 is shaped to be inserted into a connector 3 of this invention so that a continuous, undistorted electrical signal may be transmitted from the electrode 2 though the connector 3 and cable 4 to recorder 6 as previously shown in FIG. 1.

Connector 3 is shown in FIG. 2 as a housing 11, an attached closure member 12 and a clamp means 14 within the assembled housing 11 and closure member 12 for accepting and retaining tab 10 in electrical contact with the connector. The housing 11 has a front opening 13 leading to the open front end between lower jaw 15 and upper jaw 16 of clamp means 14.

The housing 11 comprises a base 23 which supports the clamp means, a roof 24 with a rearward opening slot 27, and two side members 25, each joining a lateral edge of a roof 24 and the corresponding lateral edge of base 23. A slide plate 19 and attached finger movable member 20 together comprise a slide actuator 26. The slide plate 19 slides on or beneath the lower surface of the roof 24, and finger-movable member 20 rides in slot 27 between a front and a rear position. In its front position, it forces the upper jaw 16 downward to compress the tab 10 between jaws 15 and 16. In the rear position depicted in FIG. 2, the jaws are separated from each other in an open position. A transverse ridge 21 is shown in the base to assist in gripping the connector while moving member 20 of the slide actuator.

Figure 3:
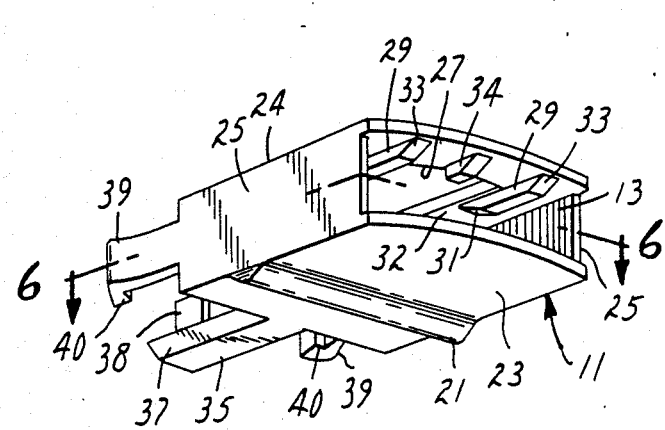
FIG. 3 is a perspective view of the housing of the invention.

FIG. 3 shows some of the details of an embodiment of the housing 11 of this invention. The base 23, roof 24 and side members 25 are shown. The roof 24 has a rearward opening slot 27 through which the finger-movable member 20, not shown, passes. Guide ribs 29 are shown integrally formed on the underside of roof 24. Each rib has a generally planar lower surface 30 and an angular transition area 31 to the rear of planar surface 30. Transition area 31 comprises a forwardly directed, downwardly angled ramp connecting a generally planar area 32 on the underside of the roof 24 and rearward of the transition are to the planar lower surface 30. In this embodiment the guide ribs 29 together with the planar surface 32 to the rear of ribs 29 comprise the slide actuator guide means. In operation, slide plate 19 of the slide actuator, not shown in this drawing, is actuated to move from a rear position where it is in contact with generally planar surface 32 to a lower position in contact with lower surface 30 of the ribs 29.

Figure 7:
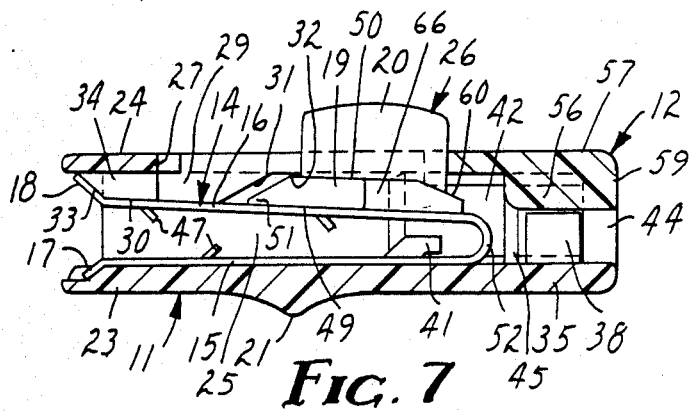
FIG. 7 is a cross-sectional side view of the housing taken along line 7—7 of FIG. 6, and further illustrating the clamp means and slide actuator of the invention shown in full, with the jaws in an open, unclamped position.
Figure 8:
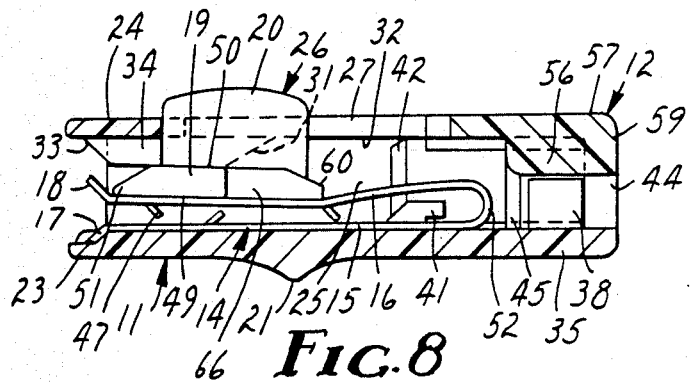
FIG. 8 is a cross-sectional side view of the housing corresponding to FIG. 7, showing the clamp means and slide actuator in full in the closed, electrode retaining position.

As more clearly shown in FIGS. 7 and 8, the slide plate 19 has a forwardly-directed, downwardly sloped front edge 51. This front edge 51 slides against the ramp of the transition area 31 to move the slide plate 19 up and down as it is motivated backward and forward, respectively. Preferably, the angle of slope on the front edge 51 is 20-50 degrees from horizontal and is approximately the same angle as that of the matching guide means ramp 31. FIG. 3 also shows ribs 29 with sloped front ends 33 for receiving upper jaw 16 when it is in the open position. An additional support member 34 which also has a sloped front end is depicted.

In this embodiment, a rearward extension 35 of base 23 mates with closure member 12. The extension is shown with angled planar sides 37, and with cable guide members 38. Extending rearward from each side member 25 is a latch extension 39 with notch 40. Notches 40 interlock with matching indentations on the closure member 12, holding the closure member 12 and housing 11 tightly together, but permitting their separation when desired.

Figure 4:
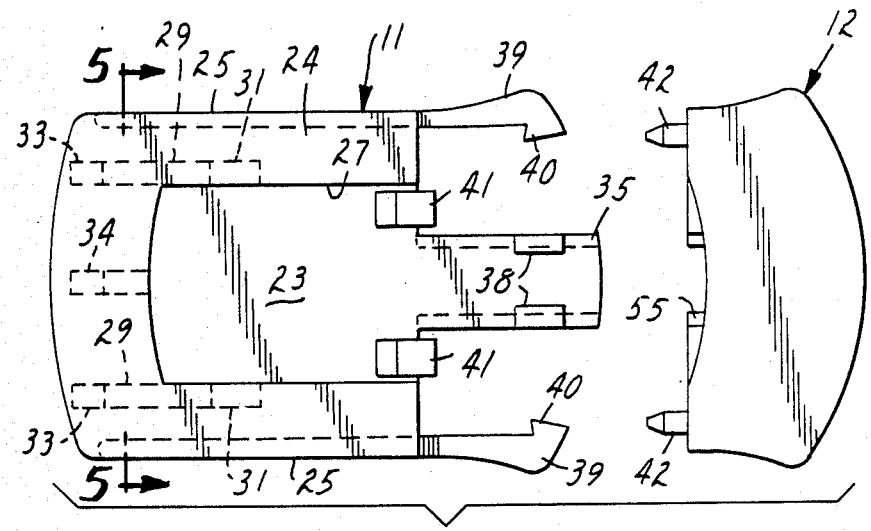
FIG. 4 is a plan view of the housing and a detached closure member of the invention.

Turning now to FIG. 4, housing 11 and closure member 12 are shown in plan view. Roof 24 is shown with rearward opening slot 27. Ramps 31 and sloped front ends 33 of guide ribs 29 are depicted by hidden lines. Support member 34 is likewise shown. Base 23 is illustrated with rearward extension 35 with cable guide members 38 extending upwardly therefrom. Jaw positioning means 41 extends upwardly from base 23 to retain lower jaw 15 of clamp means 14 in the proper location. Closure member 12 has two arms 42 which may be pushed past notches 40, forcing latch extensions 39 on each side of housing 11 outward and permitting closure member 12 to be attached to housing 11.

Figure 5:
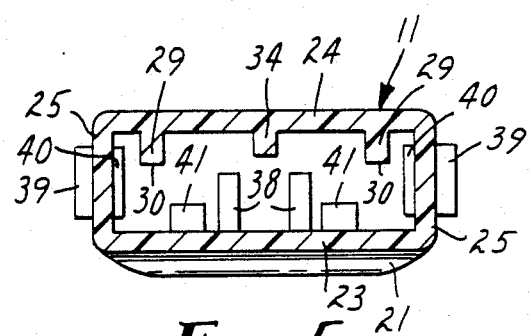
FIG. 5 is a cross-sectional front view of the housing taken along line 5—5 of FIG. 4.

FIG. 5 is a cross-sectional end view of housing 11, showing base 23 with cable guide members 38 and jaw positioning means 41 extending upwardly therefrom. Each side member 25 has a latch extension 39 and notch 40 is at the rear portion. Roof 24 has guide ribs 29 pendant from its underside. Optional support member 34 is also shown.

Figure 6:
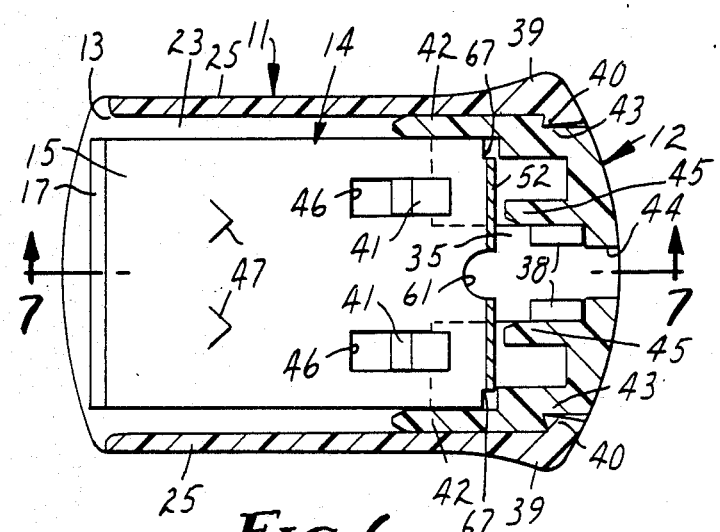
FIG. 6 is a cross-sectional plan view of the housing taken along line 6—6 of FIG. 3, together with a plan view of the closure attached to the housing and the clamp means within the housing.

FIG. 6 shows the assembly of housing 11, closure member 12 and lower jaw 15. Extending rearward from each side member 25 is a latch extension 39 with notch 40. Each of the two notches 40 interlock with an indentation 43 at the rear end of each closure member arm 42, to hold closure member 12 and housing 11 tightly together, but permitting their separation when so desired.

Closure member 12 contains aperture 44 for carrying a cable, not shown. Cable guide means 38 comprises two members attached to the rearward extension 35 of base 23. Jaw positioning means 41 and jaw retainer means 45 together act to hold the jaws 15, 16 in position. Jaw positioning means 41, shown in FIG. 6 and more clearly in FIG. 7 and is shown as two members attached to base 23 which are inserted in corresponding lower jaw apertures 46, preventing upward or outward movement of the jaws. Jaw retaining means 45, also shown in FIG. 6 and more clearly in FIGS. 7 and 8, prevents movement of the jaws rearward, by blocking such movement.

Also shown in FIG. 6 are teeth 47 on the inner surface of lower jaw 15. These teeth may be punched from the jaw member or fabricated in some other way on either or both of the jaws if so desired. These teeth project rearwardly from the surface, and resist movement of the electrode on the jaw surfaces. Other means for resisting movement may be used, including a rough-grained surface formed on the inner surface of one or both jaws 15, 16.

Lower jaw 15 is shown with a downwardly bent front end 17 which comprises a lower insertion ramp for guiding the electrode into the jaws opening. The upper jaw 16 preferably has a similar, but upwardly bent front end 18 comprising an upper insertion ramp. These upper insertion ramp 18 and lower insertion ramp 17 are more clearly shown in FIGS. 7 and 8. Preferably, these ramps are between 20 and 60 degrees from the horizontal plane, for guiding an electrode into the spaced jaw opening.

FIG. 7 shows the invention with the upper jaw 16 in the normally open position, and FIG. 8 shows the upper jaw 16 pivoted downward towards the lower jaw 15 in the closed, electrode retaining position. The lower and upper jaws, 15 and 16, are joined at their rear ends by flexible, resilient spring means 52 and together comprise the clamp means. Preferably, the clamp means is constructed from a single piece of spring metal by bending the metal to form the jaws 15, 16 connected by resilient spring means 52. Teeth 47 on the inner surface of both jaws are shown. The clamp means is supported along the lower surface of lower jaw 15 by base 23 and held in position by jaw positioning means 41 and jaw retainer means 45.

The lower surface 49 of slide plate 19 slides on the upper surface of upper jaw 16, while the upper surface 50 and sloped front edge 51 are moved back and forth in contact with generally planar surface 32, transition area comprising ramp 31, and lower surface 30 or guide ribs 29. Forward movement of slide actuator 26 by movement of finger movable member 20 forces the actuator downward along ramp 31 to a lower position. The actuator 26 motivates upper jaw 16 pivotably downward to an electrode retaining position. Further forward movement of slide actuator 26 on front lower planer surfaces 30 of ribs 29 frictionally locks the actuator 26 to maintain the electrode retaining position.

Preferably the upper surface of upper jaw 16 presses upward against the guide ribs 29 when the slide actuator 26 is retracted and the jaws 15, 16 are in their normally open position. The lower surface 30 of the guide ribs, while generally planar, need not be exactly parallel with roof 24. In the preferred embodiment, lower surface 30 angles slightly upward toward the front of the connector, generally matching the upward angle of open upper jaw 16. Such a slight upward angle contributes to the locking action which holds the slide actuator 26 in the forward position, and permits a wider opening between upper jaw 16 and lower jaw 15, when in the open position.

Cable aperture 44 in closure member 12 and cable guide members 38 hold a cable, not shown, in place. The cable 4 contains a conductive member, such as a wire, which is conductively attached to clamp means 14, preferably to spring means 52 or to the jaws near the rear end thereof.

FIG. 8 shows the connector in the closed, electrode retaining position, with the actuator 26 in the forward locked position. The upper and lower jaws provide planar surfaces for holding the electrode. Cable retainer 56 is a member located above the cable aperture 44 and extending forward to retain cable 4, not shown, within cable guide members 38.

Transverse ridge 21 is shown as extending downwardly across the lower surface of base 23, and assists in gripping the connector during actuation.

Figure 9:
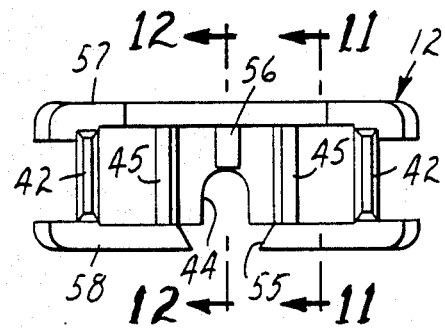
FIG. 9 is a front view of an embodiment of the closure member of the invention.

FIG. 9 shows the front end of closure member 12, having a closure member arm 42 on each side. A front-to-rear extension slot 55 holds rearward extension 35 when the closure member 12 and housing 11 are joined. Cable aperture 44 also passes through closure member 12. Cable retainer 56 above aperture 44 is as previously described. Jaw retainer means 45 project forwardly from the closure member 12 to prevent the clamp means from moving to the rear.

Figure 10:
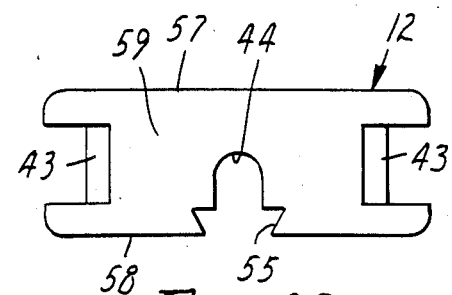
FIG. 10 is a rear view of the closure member embodiment of FIG. 9.

FIG. 10 is a rear view of closure member 12, and depicts cable aperture 44 and extension slot 55, as well as the indentation 43 along each side into which notches 40 of the housing snap to hold the closure member 12 and housing 11 tightly together.

Figure 11:
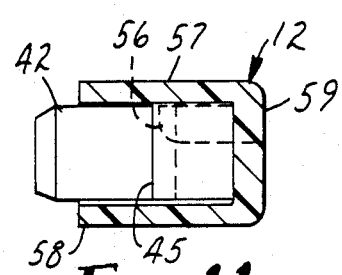
FIG. 11 is a cross-sectional side view of the closure member of FIG. 9, taken along line 11—11.
Figure 12:
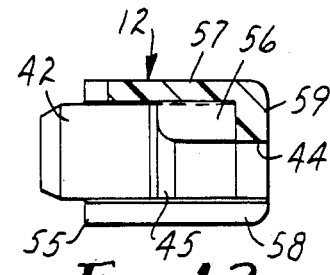
FIG. 12 is a cross-sectional side view of the closure member of FIG. 9, taken along line 12—12.

FIGS. 11 and 12 are cross-sectional side views of closure member 12, and show closure member top 57, bottom 58 and rear 59. Closure member arms 42 extend forwardly. Jaw retainer means 45 and cable retainer 56 are shown, and FIG. 12 shows the cable aperture 44 passing through the rear 59 of the closure member 12.

Figure 13:
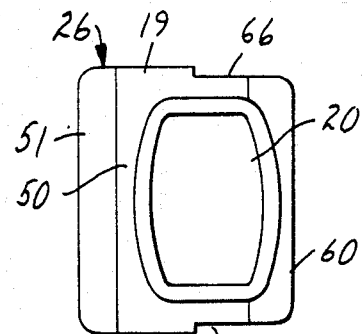
FIG. 13 is a top view of an embodiment of the slide actuator of the invention.
Figure 14:
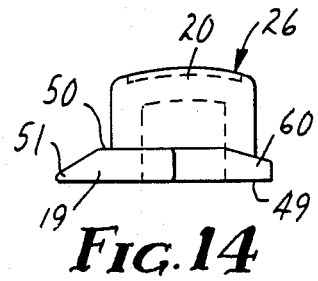
FIG. 14 is a side view of the slide actuator of FIG. 13.

The slide actuator 26 is illustrated in FIGS. 13 and 14. The actuator comprises a slide plate 19 surmounted by a finger movable member 20 adapted to slide in slot 27 in the roof 24 of the housing 11. The front edge 51 of the slide plate is angled downwardly toward the front, for sliding on corresponding ramp 31. The lower surface 49 and upper surface 50 are preferably parallel or nearly parallel and the rearmost portion 60 of upper surface 50 may be angled downwardly as shown. In FIG. 13, the opposite sides of slide plate 19, in the rear portions thereof, are indented with indentations 66 to permit passage of the slide plate between the closure member arms 42. Alternatively, the closure member arms 42 may be indented instead of the slide plate. Additional alternative constructions are possible.

Figure 15:
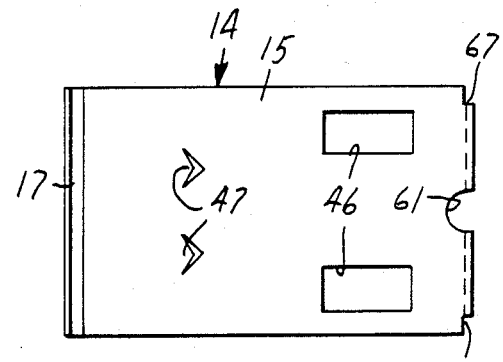
FIG. 15 is a bottom view of an embodiment of the lower jaw of the clamp means of the invention.

A bottom view of an embodiment of the clamp means is pictured in FIG. 15. Lower jaw 15 has two lower jaw apertures 46 into which fit jaw positioning means 41 of base 23. Rear apertures 61 and 67 are optional apertures for assisting in the attachment of cable 4 to the clamp means. For example, the cable end may be inserted into aperture 61 and soldered therein, or it may be wrapped around opposing corner apertures 67 and crimped, for example, to provide a conductive connection.

An alternative embodiment of the housing is shown in FIG. 16. This embodiment is useful for connections with flat electrodes 2 which are untabbed. Each side member 62 has a front opening 65 extending rearwardly along the side. The lower edges 63 of the openings are contiguous with or lower than the lower jaw 15, and the upper edge 64 is spaced therefrom to provide sufficient room for insertion of the edge of the untabbed flat electrode which is wider than the connector width.

While the embodiment shown in FIGS. 3-5 depicts slide actuator guide means as the surfaces on two ribs 29 and the planar area 32 on the underside of the roof just rearward of the ribs, other constructions are also feasible. For example, the space between the two ribs, the space between the ribs and side members 25 or both spaces may be filled in to the same lower level to provide a single rib replacement member. Also alternatively, ribs 29 may be attached to side members 25 instead of the roof 24. In other embodiments, any number of ribs 29 may be used. Preferably, a plurality of two to four ribs is used as the front portion of the actuator guide means. In each case the actuator guide means comprises front and rear generally planar surfaces connected by a transition area comprising a ramp, and the rear planar surface is higher than the front planar surface.

This invention may be used with stiff surface electrodes such as those with metallic plate surfaces. The invention is particularly useful, however, for the conductive connection to relatively soft electrodes having conformable rubber, foam polymer or other similar construction. The electrode is held in place by relatively large jaw surfaces instead of the small surfaces found in alligator clips for example.

The connector of this invention can easily be made very small and with a low profile, while providing a secure physical and conductive connection. This invention enables a patient to be EKG-monitored for extended periods with reduced opportunity for disconnection during the patient's normal movements. For example a connector weighing less than 5 grams and having a thickness of only 7 mm provides about 1 square cm of surface area on each jaw for holding an electrode.

A further advantage of this invention is the reduction or elimination of accidental short circuits. The electrically active elements are protected by the housing and closure member to prevent such accidents. With an electrode inserted into the connector of this invention, it is difficult to touch the conductive members of the connector with a finger or other body member.

The connector 3 is easily attached or detached from an electrode using one hand only.

An advantage of this connector is that both the upper and lower jaws are conductive, so that the orientation of the connector to the inserted electrode is immaterial. This is important because many flat electrodes used in medical applications are generally conductive on one side only.

The dimensions of the connector can be varied for various electrode thicknesses, and for achieving a desired release force with particular electrodes. For example, prototype connectors of this invention have been made with have a release force of 4–5 pounds force (1.8–2.3 kg. force) with particular EKG electrodes with vinyl foam backing. Conventional connectors used with these electrodes have a release force of about 2 pounds force (0.9 kg. force), and easily become disconnected at inopportune times.

With the present invention, relative movement of the electrode and the connector jaws is resisted by the large surface area of the jaws which clamp the electrode. Thus, artifacts in the trace resulting from such movement are avoided.

This invention permits insertion of an electrode into a jaw opening having a height greater than the electrode thickness, avoiding scraping of the electrode surface which occurs with spring jaw connectors of the prior art.

Numerous characteristics and advantages of this invention have been set forth in the foregoing description. It will be understood, however, that is disclosure is in many respects illustrative only. Changes may be made in details, particularly in matters of shape, size and arrangement of parts without exceeding the scope of the invention. The scope of the invention is defined the appended claims.

What is claimed is:

1. A connector for removably attaching a flat electrode to a conducting cable, comprising: clamp means comprising a flat upper jaw and a flat lower jaw each having front and rear ends, said jaws comprising conductive resilient flexible sheet material and having inner facing surfaces spaced from each other at said front end for accepting and retaining a flat electrode therebetween, and joined at the opposite, rear ends by flexible resilient spring means to normally maintain said jaws in an open position, and adapted for pivotal downward movement of said upper jaw toward said lower jaw to an electrode retaining position in which said facing surfaces of said jaws resist movement of said flat electrode retained therebetween, said clamp means adapted for conductive attachment to a conducting cable;

a slide actuator, comprising a generally flat slide plate having a forwardly directed, downwardly sloped front edge and a finger movable member attached to the upper side of said plate for moving said actuator forward and backward;

a housing having a front opening and adapted to contain said clamp means and said slide actuator above said clamp means, said front opening leading to said open front end of jaws within said housing, said housing comprising
   (a) a base for supporting said clamp means;
   (b) a roof with rearward opening slot therein, said slot adapted for passage of said finger movable member therethrough;
   (c) two side members, each joining the corresponding lateral edges of said base and roof; and
   (d) slide actuator guide means at or below the underside of said roof, having front and rear generally planar lower surfaces separated by a transition area comprising a forwardly directed ramp angled downwardly from said rear surface to said front surface, wherein first forward movement of said slide actuator forces said actuator downward along said guide means ramp to motivate said upper jaw pivotally downward to said electrode retaining position, and further forward movement of said slide actuator along said front planar lower surface frictionally locks said slide actuator to maintain said electrode retaining position; and a closure member abutting the rear of said housing and attached thereto for retaining said clamp means and said slide actuator within said housing, said closure member having an aperture therethrough for carrying said cable to said clamp means.

2. The connector according to claim 1, wherein said the front generally planar surface and the transition area of the slide actuator guide means comprises a plurality of ribs integral with said roof and pendant therefrom in parallel alignment with said slot.

3. The connector according to claim 1, further comprising at least one aperture in said rear end of said lower jaw, and at least one jaw positioning means extending upwardly from said base to rest in said lower jaw aperture for maintaining the position thereof within said housing.

4. The connector according to claim 1, further comprising a transverse ridge on the outer surface of said base for gripping said connector.

5. The connector according to claim 1, wherein said conductive resilient flexible sheet material is spring metal.

6. The connector according to claim 1, wherein said clamp means is conductively attached to said conducting cable with solder.

7. The connector according to claim 1, wherein the front edge of said lower jaw is bent downwardly and the front edge of said upper jaw is bent upwardly, said downward and upward bends comprising ramps for insertion of said flat electrodes inserted between the jaws.

8. The connector according to claim 1, further comprising rough grained surfaces on one or both of said jaw inner facing surfaces for resisting movement of an electrode retained therebetween.

9. The connector according to claim 1, further comprising a plurality of rearwardly projecting teeth on one or both said jaw inner facing surfaces for resisting mvoement of an electrode retained therebetween.

10. The connector according to claim 9, wherein said teeth are electrically conductive.

11. The connector according to claim 1, further comprising slots in said side members adjacent to sides of said clamp means, said slots adapted for the insertion of an electrode therein having a width greater than the width of said connector and for removably retaining said wide electrode within said clamp means.

12. The connector according to claim 1, further comprising jaw retainer means connected to said closure member, said jaw retainer means abutting said rear end of said jaws when said closure member is attached to said housing with clamp means therein, to prevent movement of said clamp means within said housing.

* * * * *

UNITED STATES PATENT AND TRADEMARK OFFICE
CERTIFICATE OF CORRECTION

PATENT NO.   :   4,700,997
DATED        :   October 20, 1987
INVENTOR(S)  :   Jerome E. Strand It is certified that error appears in the above-identified patent and that said Letters Patent is hereby corrected as shown below:

Col. 6, line 65, "or" should read --of--.

Col. 10, line 50, "mvoement" should read --movement--.

Signed and Sealed this

Twelfth Day of April, 1988

Attest:

DONALD J. QUIGG

*Attesting Officer*         *Commissioner of Patents and Trademarks*